United States Patent
Antalffy

(10) Patent No.: US 10,561,340 B2
(45) Date of Patent: Feb. 18, 2020

(54) SPIROMETER

(71) Applicant: Smart Respiratory Products Limited, London (GB)

(72) Inventor: Thomas Antalffy, London (GB)

(73) Assignee: Smart Respiratory Products Limited, London (GB)

( * ) Notice: Subject to any disclaimer, the term of this patent is extended or adjusted under 35 U.S.C. 154(b) by 346 days.

(21) Appl. No.: 15/504,402

(22) PCT Filed: Aug. 19, 2015

(86) PCT No.: PCT/GB2015/052403
§ 371 (c)(1),
(2) Date: Feb. 16, 2017

(87) PCT Pub. No.: WO2016/027084
PCT Pub. Date: Feb. 25, 2016

(65) Prior Publication Data
US 2017/0231525 A1   Aug. 17, 2017

(30) Foreign Application Priority Data

Aug. 19, 2014  (GB) .................................. 1414731.8
Nov. 12, 2014  (GB) .................................. 1420147.9

(51) Int. Cl.
*A61B 5/09* (2006.01)
*A61B 5/087* (2006.01)
*A61B 5/00* (2006.01)

(52) U.S. Cl.
CPC .............. *A61B 5/09* (2013.01); *A61B 5/0871* (2013.01); *A61B 5/0873* (2013.01); *A61B 5/7257* (2013.01); *A61B 2562/227* (2013.01)

(58) Field of Classification Search
CPC ........ A61B 5/0871; A61B 5/0873; A61B 5/09; A61B 5/097
See application file for complete search history.

(56) References Cited

U.S. PATENT DOCUMENTS 4,282,883 A * 8/1981 Yerushalmy ............. A61B 5/09
600/539
5,388,466 A   2/1995 Teunissen
(Continued)

FOREIGN PATENT DOCUMENTS

CN   102727208 A   10/2012
EP   0084159 A1   7/1983
(Continued)

OTHER PUBLICATIONS

The International Search Report (ISR) for PCT/GB2015/052403 dated Oct. 13, 2015, pp. 1-3.
(Continued)

*Primary Examiner* — Thaddeus B Cox
(74) *Attorney, Agent, or Firm* — McDonnell Boehnen Hulbert & Berghoff LLP

(57) ABSTRACT

The chronic nature of asthma necessitates regular self-monitoring of respiratory function in susceptible individuals, however the available devices for performing the necessary measurements are either inaccurate or expensive and bulky. The present invention provides a small, cheap spirometer for efficient, accurate and convenient measurement of breathing characteristics.

23 Claims, 11 Drawing Sheets

(56) References Cited

U.S. PATENT DOCUMENTS

| | | | |
|---|---|---|---|
| 6,314,822 B1* | 11/2001 | Ford | A61B 5/0873 |
| | | | 73/861.74 |
| 2007/0059165 A1 | 3/2007 | Boschetti Sacco | |
| 2012/0029376 A1* | 2/2012 | Meng | A61B 5/087 |
| | | | 600/538 |
| 2015/0150483 A1* | 6/2015 | Mangell | A61B 5/0871 |
| | | | 600/533 |
| 2017/0119279 A1* | 5/2017 | Ahmad | A61B 5/74 |

FOREIGN PATENT DOCUMENTS

| | | |
|---|---|---|
| EP | 0 505 450 | 11/1995 |
| GB | 2024628 A | 1/1980 |
| GB | 1602630 A | 11/1981 |
| GB | 2224567 A | 5/1990 |
| JP | 2000 298043 | 10/2000 |
| WO | 1991/08703 | 6/1991 |
| WO | 2013/184066 | 12/2013 |
| WO | 2013/184066 A1 | 12/2013 |

OTHER PUBLICATIONS

The Written Opinion of the International Searching Authority for PCT/GB2015/052403 dated Oct. 13, 2015, pp. 1-5.
Combined Search and Examination Report in GB1414731.8, dated Feb. 15, 2015.
Combined Search and Examination Report in GB1420147.9, dated Mar. 31, 2015.

* cited by examiner

SPIROMETER

FIELD OF THE INVENTION

The present invention relates to a spirometer adapted to be used in measuring respiratory function and more particularly, a spirometer device which incorporates an electrical network which provides functional advantages to the user when measuring peak expiratory flow.

BACKGROUND TO THE INVENTION

Hundreds of millions of people suffer from chronic respiratory diseases. According to the latest World Health Organisation (WHO) estimates (2011), currently 235 million people have asthma, 64 million people have chronic obstructive pulmonary disease (COPD) and millions have other often-underdiagnosed chronic respiratory diseases.

Accurately measuring breathing capacity is important in the management of asthma and other respiratory conditions and in particular in predicting (and controlling) asthma attacks in susceptible individuals. During an acute asthma attack, the muscles of the upper airways contract, resulting in the partial or complete obstruction of the airways and making it harder for the lungs to take in and release air. However, narrowing of the airways is not confined to the onset of the attack, but rather builds up gradually over time. Often bronchial inflammation, causing a narrowing the airways, may have begun some time before the first symptoms of asthma are felt by the individual. A range of effective anti-asthma drugs are available which can substantially limit or eliminate such attacks, but these must be administered appropriately to avoid negative effects associated with inappropriate dosage.

The chronic nature of asthma therefore necessitates regular monitoring of respiratory function in susceptible individuals to detect symptoms which are prognostic of bronchial inflammation as early as possible and for practical reasons typically involves a combination of self-assessment and periodic assessment by a clinician.

It is well established that measurement of peak expiratory flow rate (PEF) usually measured in litres per minute, which indicates the speed with which air is blown out of the lungs, provides a reliable indication of respiratory function (Global strategy for asthma management and prevention. Bethesda (Md.): Global Initiative for Asthma, 2012). Simple mechanical devices are known for this purpose such as Peak Flow Meters (PFMs). These devices are simply constructed and typically consist of a plastic tube with a mouthpiece on one end.

In use, when a patient exhales into the mouthpiece of the tube, the force of the expiratory flow causes an opposing and reciprocating plate and an externally visible marker or pointer, often located in a channel or groove within the tube, to be impelled from a resettable start position (or zero) to a position corresponding to the maximum, or peak, expiratory flow of a single exhalation. Commonly, the PFM will incorporate a calibrated scale adjacent to the marker so that the individual can visualize and manually record the peak expiratory flow of that exhalation as indicated by the distance traveled by the marker along the scale. Repeated measurement of this kind is made in order to monitor changes in lung function, such as those that might be result from asthma or other respiratory ailments.

Some examples of PFMs incorporate an elastic device, such as a spring, to return the plate, moveably arranged within the tube, to the starting position as the force of the expiratory flow declines from a maximum value and becomes unequal to the elastic force of the spring, the opposing force of the spring returns the moveable plate towards its starting position. The marker, however, not being connected to the movable plate, remains at the location of maximum movement from the starting position, indicating the maximal distance moved by the plate during that expiration, allowing peak expiratory flow to be calculated.

PFMs which are currently available have a number of limitations. Firstly, the utility of PFMs is limited by their size, which makes inconspicuous transport or use difficult. As a result, the ability to monitor respiratory function at the required times can compromised.

Secondly, PFM devices generally require the results of tests to be taken, recorded and interpreted manually by the user at periodic intervals which leads to inaccuracies in the recordation of breathing characteristics and a failure to record results consistently over an extended period. This can adversely affect the diagnosis of individual risk factors which is a fundamental consideration in determining appropriate treatment regimens for a patient.

Thirdly, the process of taking and recording the readings can be time-consuming, which in combination with often cumbersome equipment required for analysis, frequently results in a disinclination on the part of the patient to make regular measurements of PEF. Poor adherence to the monitoring regimen, giving rise to sporadic datasets is a major problem in effective asthma management.

Fourthly, the PFM does not enable any more advanced monitoring of breathing function other than a measure of PEF.

More advanced devices are known, such as that marketed by MIR (http://www.spirometry.com/) in which a disposable turbine spirometer is used in conjunction with a proprietary monitoring system which optically monitors the rotation rate of the turbine when the passage of air causes it to rotate. However, these devices are expensive and bulky. The result is that the aforementioned system does not lend itself to use by individuals and as a consequence it is generally used by medical practitioners.

With the above in mind, the present invention has been devised. The invention seeks to improve the efficiency, accuracy, reliability and convenience of the self-assessment of respiratory function in susceptible individuals, particularly the monitoring of peak expiratory flow for the purposes of asthma management.

SUMMARY OF THE INVENTION

Advantageously, the invention provides a spirometer which facilitates accurate measurement and recordation of Peak Expiratory Flow (PEF or PEFR), Forced Expiratory Volume (FEV), Forced Expiratory Flow, (FEF) and Forced Vital Capacity (FVC); key respiratory parameters in the diagnosis and management of chronic respiratory conditions. The small size of the spirometer enables it to be easily transported and provides the individual with the means for more convenient and efficient self-assessment than has hitherto been possible. By virtue of the above features the spirometer is small, robust, accurate and has a low construction cost compared with existing devices capable of measuring the aforementioned parameters. In a preferred embodiment, the spirometer does not feature meshes or screens within which bacteria or other such contaminants may become trapped and accordingly permits hygienic use and straightforward sterilisation and maintenance.

The present invention also provides a spirometer for use in measuring throughput air flow comprising; a spirometer body having a cylindrical wall defining a cavity and having one or more windows arranged to admit ambient light to the cavity; one or more deflectors configured to cause an airflow input to the cavity defined by the spirometer body to rotate; a rotor arranged inside the cavity defined by the spirometer body to be caused to rotate responsive to the rotating air flow; and one or more photodetectors, arranged at the wall of the spirometer body facing into the cavity to detect an amount of light incident thereon inside the cavity; wherein the spirometer is configured such that, as the angle of the rotor changes as it rotates, the amount of the ambient light admitted to the cavity by the one or more windows and conveyed to the or each photodetector is varied due to obstruction by the rotor; and wherein the one or more photodetectors form part of an electrical network configured to, in use, provide an electrical signal useable to detect the rotation rate of the rotor.

It will be appreciated that in embodiments of the above aspect of the present invention, when in use the interruption of ambient light by the rotary motion of the rotor in response to input or output air flow, be sensed by a photodetector and transduced into an electrical signal useable to detect the rotation of the rotor. In preferred embodiments of the invention, the photodetector is a photodiode configured to detect ambient light inside the cavity of the spirometer. Preferably, upon illumination the photodetector produces a voltage and supplies an electric current, which will vary according to the amount of illumination incident on it. Preferably, such a current will be proportional to the incident light intensity. In addition to photodiodes, photodetectors of the present invention may include, but are not limited to photoresistors, light dependent resistors (LDR), phototransistors, LEDs which are reverse-biased to act as photodiodes, photovoltaic cells, solar cells, photomultiplier tubes, phototubes, quantum dot photoconductors, active-pixel sensors (APSs), charge-coupled devices (CCD), optical detectors, such as microbolometers, pyroelectric detectors, thermocouples and thermistors.

Conductive coatings are prone to wear over time and can result in a reduced lifetime of the spirometer. Consequently, spirometers of the present invention which use optical detection of rotation beneficially have greater durability. In addition to greater durability, spirometers of the present invention which use optical detection of rotation beneficially allow for more accurate measurements of breathing characteristics than embodiments of the invention where conductive coatings are used to generate a switched conductive path. Consequently, spirometers of the invention featuring photodetectors may advantageously be used to measure and record key lung function parameters for those with chronic respiratory conditions over time such as Forced Vital Capacity (FVC) accurately (total volume exhaled air), which permits assessment of both obstructive and restrictive lung function impairment in addition to PEF. Spirometers of the invention featuring photodetectors may also advantageously be used to measure and record FEF25, FEF50 and FEF75 (Forced Expiratory Flow at 25%, 50% and 75% volume expired air). The mean flow between the points FEF25 and FEF 75 is a critical parameter (called the FEF2575), since this is actually the first parameter that demonstrates a decline in many respiratory diseases. Additionally, spirometers of the invention which feature optical detection of rotation may be used to measure FEV1/FEV6; the ratio of the amount of air exhaled in one second and six seconds, which operates as a sensitive and specific test for the diagnosis of airway obstruction and which is also frequently used by physicians to indicate lung function in transplant patients.

The invention also provides a spirometer wherein the electrical network is connected to one or more contacts of a phone plug that is coupled to, or preferably rigidly connected to the spirometer. In a preferred embodiment the electrical network of the spirometer is connected to one or more contacts of a phone plug. Preferably, the electrical network of the spirometer will be connected to one or more contacts of a 3.5 mm four-contact "Tip", "Ring", "Ring", "Sleeve" (TRRS) phone plug. However, it is envisaged that the electrical network of the spirometer will function equally well with other types of phone plug such as, for example, 2-contact, TS and 3-contact, TRS connectors. In alternative embodiments the electrical network may be connected to two or more, three or more, four or more, five or more, six or more, seven or more, eight or more, nine or more or ten or more contacts of a suitable phone plug.

Preferably, the phone plug is arranged so as to be rigidly connected to the spirometer. Alternatively, however, the phone plug may be flexibly coupled to the spirometer, for example, using an electrical cable or similar means known in the art. The connection of the electrical network of the spirometer to one or more contacts of a phone plug enables the electrical signal provided by spirometer to be communicated to, processed by and stored on an electronic device such as a smartphone. Such a connection will commonly be established using the microphone input of an electronic device and will allow processing, calibration and interpretation of the electrical signal generated by the spirometer to be carried out on the electronic device. Examples of this include performing a Discrete Fourier Transform (DFT) or Fast Fourier Transform (FFT) to analyse the waveform and spectrum of the audio signal on a spectrogram. The person skilled in the art will be aware of a number of appropriate software packages or applications for processing and/or interpreting the electrical signal output generated by the spirometer and it would be regarded as routine to select a compatible or appropriate package or application, depending on the electronic device and the type of analysis to be carried out. Suitable packages include but are not limited to "Praat", "SimpleFFT", "Spectral Audio Analyzer", "TRA Audio analyzer", "AudioTool", "SPL and Spectrum Analyser", "SPL Meter" and "FFT".

In a preferred embodiment of the invention the phone plug will be connected to an electronic device such as a mobile telephone, smartphone or tablet, in order that convenient storage, visualisation, interpretation and interrogation of the electronic signal is possible by the patient and the clinician. Preferably, the phone plug will connect the spirometer to a smartphone by an audio input. The connection of the electrical network to one or more contacts of a phone plug enables fast, accurate and efficient measurements. Additionally, there is no need for users to record time, date and measurement values manually. These capabilities encourage frequent use of the device, allowing a more detailed and accurate assessment of PEF over time and facilitate greater communication between patients and physicians.

The invention also provides a spirometer wherein the rotor comprises a vane portion rigidly connected to a shaft portion such that the vane portion can rotate about an axis defined by the shaft portion; and wherein the end portions of the shaft are pivotably mounted in respective sockets of the spirometer, such that the vane portion is mounted to rotate in the rotating airflow.

The configuration of the rotor to vary the amount of ambient light incident on the one or more photodetectors depending on the position of the rotor in the cycle allows the one or more photodetectors to operate as switches dependent on the amount of illumination incident on them, permitting a switching rate to be determined. The switching rate can then be used to determine the rotation rate of the vane. Preferably, the contacts of the electrical network will switch once per rotation of the vane portion. However, equally effective constructions are envisaged which incorporate more than one switch per rotation of the vane.

In another embodiment the invention comprises a spirometer wherein the rotor comprises a vane portion rigidly connected to a shaft portion such that the vane portion can rotate about an axis defined by the shaft portion; and wherein the end portions of the shaft are pivotably mounted in respective sockets of the spirometer, such that the vane portion is mounted to rotate in the rotating airflow. It has been found that the above is a simple method of construction which enables the spirometer to be produced quickly and cheaply and yet make accurate measurements of key respiratory parameters.

The vane portion may be rigidly connected to the shaft portion such that both vane and shaft portions are caused to rotate responsive to rotating airflow, however, this arrangement is not essential and the vane and shaft portions may be connected in such a way that the shaft portion merely provides supporting means for the vane portion as it is caused to rotate in the rotating airflow.

In preferred embodiments the electrical network of the spirometer comprises one or more photodetectors arranged partially around the periphery of the rotational edge of the vane portion. Commonly, the present invention comprises a single photodetector. However, it will be appreciated that spirometers of the present invention may comprise more than one photodetector. Alternatively, spirometers of the present invention may comprise more than two photodetectors, more than three photodetectors, more than four photodetectors, more than five photodetectors, more than six photodetectors, more than seven photodetectors, more than eight photodetectors, more than nine photodetectors or more than ten photodetectors.

The one or more photodetectors are arranged at the wall of the spirometer body facing into the cavity to detect an amount of light incident thereon inside the cavity. In the context of the invention "arranged at the wall" encompasses various arrangements of photodetectors. In particular, "arranged at the wall" encompasses, but is not limited to photodetectors located on, in or adjacent the wall of the spirometer body. The one or more photodetectors are preferably arranged partially around the periphery of the rotational edge of the vane portion. Ideally, the photodetectors are located on or in recesses in the cylindrical wall defining the cavity of the spirometer. In preferred arrangements, the one or more photodetectors are located in recesses in the wall of the spirometer body facing into the cavity. This arrangement advantageously allows the free rotation of the vane within the cavity.

In preferred embodiments, the present invention provides a spirometer wherein the cavity of the spirometer body defines a first radius and the radial extent of the vane defines a second radius; and wherein the second radius is such as to allow it to block light within the cavity from reaching the one or more photodetectors but less than the first radius allowing free rotation within the cavity. Ideally, the radial extent of the vane closely approximates the radius of the cavity, so that the rotor presents a large surface area for rotating throughput air to act on and is thus able to translate the energy of the rotating air into rotation most efficiently. The rotating input or output air causes the vane to rotate resulting in an accurate measurement of breathing characteristics manifested in the rotation of the vane. Advantageously, a close approximation of the radii of the vane and that of the cavity means that, in use, during rotation, as the vane interposes between the one or more photodetectors and the one or more windows at various points during the rotation cycle, at certain rotation angles it obscures the one or more windows from the one or more photodetectors and results in blockage of a portion of ambient light from reaching one or more of the or each of the photodetectors whereas at certain other rotation angles the vane does not obscure the window and ambient light is allowed to pass to one or more of the or each of the photodetectors. This permits the rotation rate of the rotor, and therefore the passage of throughput air to be detected, whilst permitting free rotation of the vane in response to throughput air. Preferably, the present invention provides a spirometer wherein the axial extent of the or each window is less than and contained within the axial extent of the rotor. This arrangement allows light to be blocked from the one or more photodetectors when the vane interposes between the one or more photodetectors and the one or more windows. Of course, it will be appreciated that many different axial extents which are less than that of the cavity are possible whilst retaining the functionality of the spirometer. Indeed various rotor constructions are possible, where the vanes of the rotor are not of equal axial length and/or even spacing around the axis of the rotor. Preferably the vane portion extends substantially along a single plane. However, in preferred embodiments of the invention, the axial extent of the rotor is substantially the same as the axial extent of the cavity. More preferably, the vanes are of equal axial length. Even more preferably, the vanes are evenly spaced around the axis of the rotor. Still more preferably, the vanes are opaque, ensuring that during interposition of the vane between the one or more windows and the one or more photodetectors, ambient light is obscured efficiently from the one or more photodetectors.

Ideally, a spirometer of the invention has a cylindrical wall which comprises a single window and a single photodetector. However, it will be appreciated that spirometers of the present invention may comprise more than one window. Alternatively, spirometers of the present invention may comprise more than two windows, more than three windows, more than four windows, more than five windows, more than six windows, more than seven windows, more than eight windows, more than nine windows or more than ten windows. By single window it is meant single tangential window but it will be appreciated that this may also encompass several axially adjacent windows. The same is also true for photodetectors.

Advantageously, in addition to providing a rate of vane rotation, preferred embodiments of the invention also provide directional sensitivity. Determination of the direction of rotation in response to throughput airflow enabling the airflow characteristics of inhalation to be distinguished from those associated with exhalation. This feature enables more accurate measurements of user breathing characteristics to be made. In order to determine the direction of rotation, it is essential that the one or more windows and the one or more photodetectors of the spirometer are arranged such that the angle subtending between the centre of the window and the centre of the or each photodetector is less than 180 degrees. In other words, at least one of the one or more windows and at least one of the one or more photodetectors are not diametrically opposed from one another. In addition to their relative 'offset' from 180 degrees, particularly where only one photodetector is provided, it is preferable that at least one of the one or more windows and at least one of the one or more photodetectors which are offset from one another are of different dimensions. Preferably they are of differing axial or angular extents. The one or more photodetectors may be smaller or larger than the one or more windows. In preferred embodiments the one or more windows is rectangular or square. Preferably, at least one of the one or more windows are larger than the one or more photodetectors, however, it will be appreciated that windows may be different shapes, for example a triangle. Preferably, the one or more windows are each between 0.5 and 5 $cm^2$ sq, between 0.5 and 4 $cm^2$ sq, between 0.5 and 3 cm sq, between 0.5 and 2 $cm^2$ sq, or alternatively are each between 0.5 and 1 $cm^2$ sq. It will also be appreciated that arrays of windows and/or photodetectors may be used in embodiments of the present invention as desired. Consequently, in another embodiment the present invention provides a spirometer, wherein the cylindrical wall comprises a single window or more than one axially adjacent windows and one or more photodetectors; and wherein the angle subtending between the centre of the window and the centre of the or each photodetector is less than 180 degrees. Typically, the angle subtending between the centre of the window and the centre of the or each photodetector is less than 170 degrees, but may be less than 160 degrees, less than 150 degrees, less than 140 degrees, less than 130 degrees, less than 120 degrees, less than 110 degrees, less than 100 degrees, less than 90 degrees, less than 80 degrees, less than 70 degrees, less than 60 degrees, less than 50 degrees, less than 40 degrees, less than 30 degrees, less than 20 degrees or alternatively less than 10 degrees.

In another embodiment the present invention provides a spirometer, wherein a single photodetector is provided and a single window is provided and the angle between opposing edges of the window and the photodetector is 180 degrees or greater. Optionally, in embodiments of the invention where detection of the direction of rotation is desired, the window is of different dimensions to the photodetector, preferably the window will be larger across its axial extent than the photodetector.

In an alternative embodiment the invention provides a spirometer, wherein the angle subtended by the window is greater than the angle subtended by the or each photodetector, and optionally wherein the axial extent of the window is uniform across its angular extent.

The invention also provides a spirometer which is capable of distinguishing the characteristics of throughput air due to inhalation and exhalation. In such embodiments, the spirometer may feature a window wherein the axial extent of the window varies across its angular extent, optionally uniformly from one edge to the other. Various shapes of window where the axial extent of the window varies across its angular extent are envisaged which will function to provide directional sensitivity. Preferably, the window is triangular in shape.

Optionally, the cylindrical wall comprises a single window and more than one photodetector. Preferably, the plural photodetectors are spaced at angles around the cylindrical wall.

In all embodiments of the invention relying on optical detection of the rotation of the rotor, a spirometer is provided wherein the cylindrical wall of the spirometer is opaque except for the one or more windows arranged to admit ambient light to the cavity. Usually, the housing will be made of opaque plastics material. Ambient light is the preferred source of light and is admitted to the cavity of the spirometer by one or more windows. Preferably, no active or powered light source is provided as part of the invention.

The present invention also provides a spirometer, wherein the electrical network further comprises one or more resistors. Preferably, the one or more resistors are in the range 500 Ohm-3 k Ohm and in serial connection with the rotor. Preferably, at least one of the one or more resistors is a 1 k Ohm resistor. Preferably, the electrical network comprises two or more resistors. Still more preferably, the electrical network comprises 3 resistors. In the context of the present invention the resistor functions in conjunction with the electrical network and electronics controlling electrical signals received at the microphone input to compensate for the switching response provided in many smartphones below certain resistances as a means to remotely control smartphone functionality i.e. imposing a load on the circuit via the incorporation of a resistor may be necessary in order to circumvent the small resistance direct contact response of an associated electronic device below a certain resistance. For example, many smartphones have audio inputs which are calibrated to be responsive to signals below 100 Ohm, 200 Ohm, 300 Ohm, 400 Ohm, 500 Ohm, 1 k Ohm, 1.5 k Ohm, 2 k Ohm or 3 k Ohm such that certain applications (e.g. answering incoming calls) are triggered by small resistance direct contacts. Consequently, the resistor is preferably in serial connection with the rotor and applies a fixed resistance such that it is compatible with the electronic device envisaged for use. The additional resistance in the circuit allows the electronic device to process input signals as normal. Although this could be achieved in the absence of a resistor, preferred embodiments of the invention the electrical network comprise one or more resistors in the range 500 Ohm-3 k Ohm or 1 k Ohm-3 k Ohm. More preferably, the electrical network comprises one or more resistors in the range 1 k Ohm-2 k Ohm. Ideally, the electrical network comprises a 1 k Ohm resistor in serial connection with the rotor. It will be appreciated however, that the same effect could be achieved with larger resistor, for example a 1.5 k Ohm, 2 kOhm, 3 kOhm, 4 kOhm, 5 k Ohm, 6 k Ohm, 7 k Ohm, 8 k Ohm, 9 k Ohm or 10 k Ohm resistor. Similarly a combination of resistors may be used to achieve the desired resistance in the circuit. Advantageously, the resistor is constructed of metal wire or a carbon composite, since these are very cheap to produce, however, in certain embodiments where greater precision is required, other types of resistor may be more suitable.

Also provided is a method of measuring throughput air flow using a spirometer as claimed in any preceding claim, comprising the steps of: connecting the spirometer to an electronic device; and detecting, using the electronic device, the electrical signal provided by the spirometer experiencing the airflow therethrough; and processing, using the electronic device, the electrical signal to obtain a measurement of a characteristic of the throughput airflow. Preferably, processing, using the electronic device, the electrical signal comprises determining a rotation rate of the rotor from a component of the electrical signal produced by the operation of the one or more photodetectors as the rotor rotates. More preferably, processing, using the electronic device, the electrical signal further comprises the step of performing a Discrete Fourier Transform (DFT) to convert a component of the electrical signal produced by the operation of the one or more photodetectors as the rotor rotates into a rotation rate. Still more preferably, processing, using the electronic device, the electrical signal comprises determining characteristics of the airflow from a determined rotation rate of the rotor, based on calibration data defining relationships therebetween for the spirometer. Advantageously, processing, using the electronic device the electrical signal further comprises determining the direction of rotation of the rotor. This allows the characteristics of inhalation and exhalation to be distinguished.

Although each individual spirometer of the present invention will have different characteristics and features, using exhalations of various force the maximum signal frequency, maximum vane rotation rate, Peak Expiratory Flow Rate (PEF or PEFR), Forced Expiratory Volume (FEV), Forced Expiratory Flow, (FEF) and Forced Vital Capacity (FVC) may be calculated for each individual spirometer. In the present invention, the relationship between signal frequency and peak flow rate determined from the spectral analysis of the microphone input is defined by a linear relationship. The existence of a linear relationship between these two parameters within a normal range means that conversion from a maximum signal frequency to a Peak Expiratory Flow (PEF) rate which is useable by the patient (i.e. a value in litres/minute) requires the application of a simple multiplier. The linear conversion of the peak harmonic frequency generated by the spirometer into flow rate described above will normally be performed automatically by one or more suitable software packages, providing an output peak flow rate which is useable by the patient.

Optical detection allows a more sensitive detection of various respiratory parameters, such as Peak Expiratory Flow Rate (PEF or PEFR), Forced Expiratory Volume (FEV), Forced Expiratory Flow, (FEF) and Forced Vital Capacity (FVC). The relationship between these respiratory parameters is well established and may be derived from a graphical output of signal measurements derived from an exhalation (above x-axis) and inhalation (below x-axis) using a spirometer of the invention. The exhalation produces a line which rises sharply and declines gradually. In contrast, the inhalation (below the x-axis) produces a more rounded profile. Measurement of the direction of vane rotation provides a more accurate method of determining whether the values obtained relate to exhalation or inhalation. A number of diagnostic values can be calculated from analysis of such an output.

Raw signals, signal spectrum and signal intensity are measured. At high revolutions signal processing by Discrete Fourier Transform (DFT) is used to determine rotations per second. At low revolutions the signal intensity is used to determine individual on-off signals. Detection of direction of rotation optimally occurs where the signal is strongest (rotation is fastest) in the inhale-exhale cycle.

It will be appreciated that the relationship between signal frequency and peak flow rate, although linear in the normal range, need not under all circumstances be linear. A margin of error exists at very low and very high flow rates outside the normal range, where the rotational response of the vane to throughput airflow is limited by inertia or maximum rotation respectively. However, this margin of error may be limited by rigorous calibration of each individual spirometer.

In addition to detecting, analysing and processing the signal peak of the dominant harmonic, the one or more software packages used in the present invention may detect and utlilise additional peaks present in the signal output in order to determine the signal frequency of the dominant harmonic with greater accuracy and precision. These peaks for example, may include, but are not limited to those at 0.5×, 1.5×, 2×, 2.5×, 3×, 3.5×, 4×, 4.5× and/or the frequency of the dominant harmonic. Software packages to be used in the present invention may apply a DFT or FFT to divide the spectrum between 0 and the sampling frequency into bands in order to improve the accuracy of the measurement. Preferably, an FFT will be applied. More preferably, the spectrum will be divided into equally sized bands. Even more preferably, the signal will be graphed using the Praat software package and subsequent analyses (e.g. application of FFT) performed using Microsoft Excel.

Statistical analysis of other characteristics of the spectral output (e.g. the area under the graphed flow rate line) may be used to determine other useful breathing characteristics as desired.

Finally, the present invention also provides a method of manufacturing a spirometer for measuring throughput air flow, comprising: providing a spirometer body having a cylindrical wall defining a cavity and having one or more windows arranged to admit ambient light to the cavity; providing inlet and outlet deflectors configured to cause an input airflow to the cavity defined by the spirometer body to rotate and a rotor comprising a vane portion rigidly connected to a shaft portion; providing one or more photodetectors arranged at the wall of the spirometer body facing into the cavity to detect an amount of light incident thereon inside the cavity; forming part of an electrical network coupled to the or each photodetector and configured to, in use, provide an electrical signal useable to detect the rotation rate of the rotor; assembling the rotor between the inlet and outlet deflectors such that the end portions of the shaft are pivotably mounted in respective sockets defined at the radial centre of the deflectors, such that the vane portion is mounted to rotate in the rotating airflow such that, in use as the angle of the rotor changes as it rotates the amount of the ambient light admitted to the cavity by the one or more windows and conveyed to the or each photodetector is varied due to obstruction by the rotor; and coupling or rigidly connecting a phone plug to the spirometer and connecting the electrical network to one or more contacts of the phone plug that is coupled to or rigidly the spirometer.

It has been found that the above method of construction provides a quick, straightforward and economical method of manufacture of an effective, accurate, cheap and convenient spirometer.

BRIEF DESCRIPTION OF THE FIGURES

The invention will now be described in detail with reference to specific embodiments and with reference to the accompanying drawings, in which:

FIG. 9 shows a perspective view of a deflector of the invention. The deflector show is designed with curved spokes to cause the input air to rotate in the cavity of the spirometer defined by the cylindrical wall, rather than to flow straight through.

DETAILED DESCRIPTION

Figure 1:
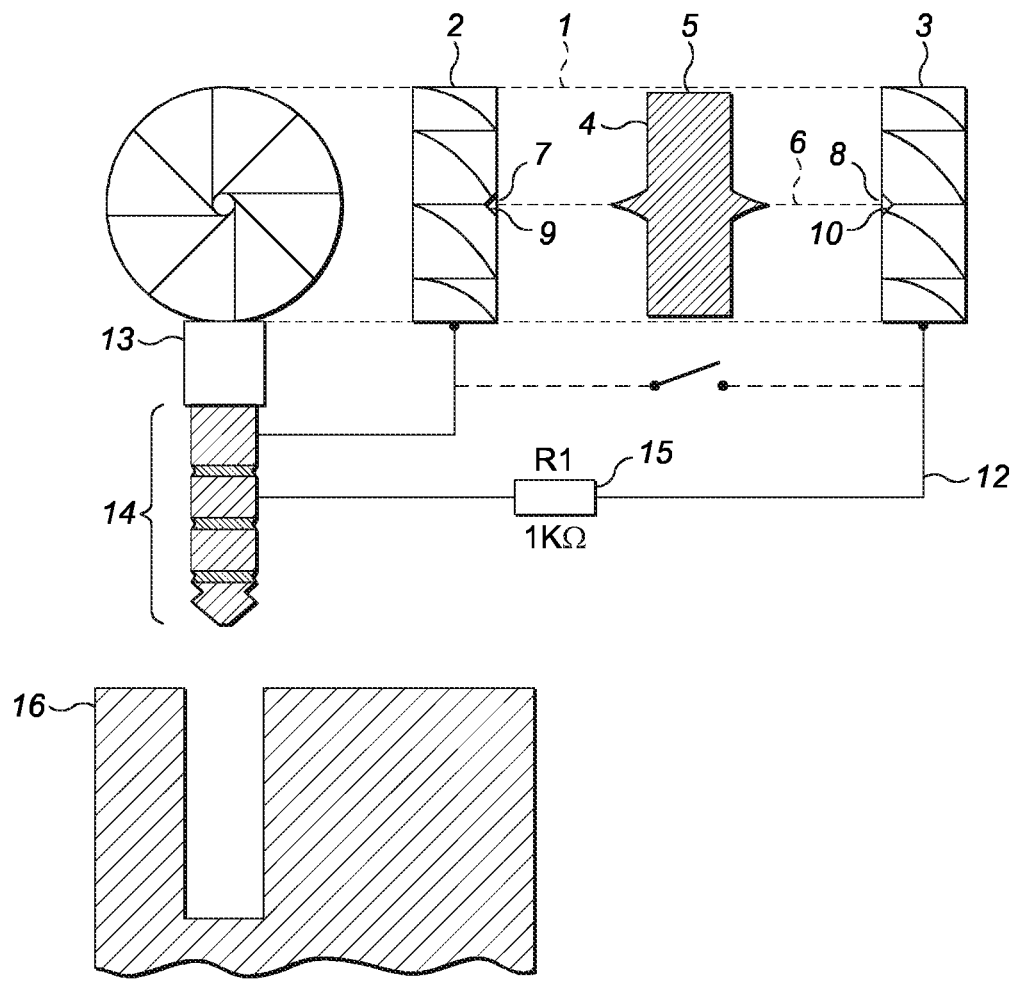
FIG. 1 shows a longitudinal section of a spirometer (not claimed) with a simplified circuit diagram of the electrical network comprised in the spirometer.
Figure 2:
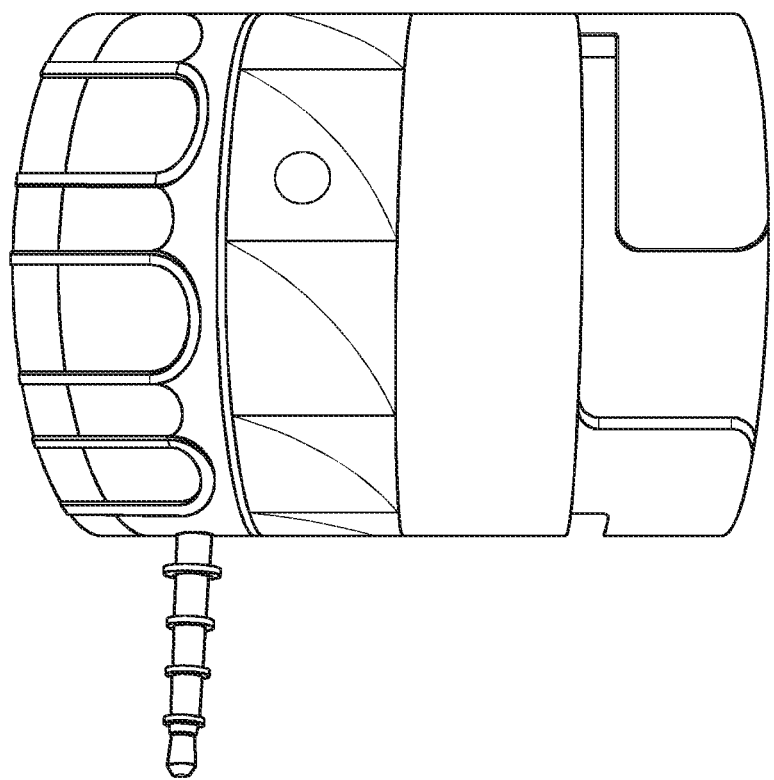
FIG. 2 shows a photograph of an assembled spirometer device (not claimed) incorporating a 4-conductor (TRRS) phone plug.
Figure 3:
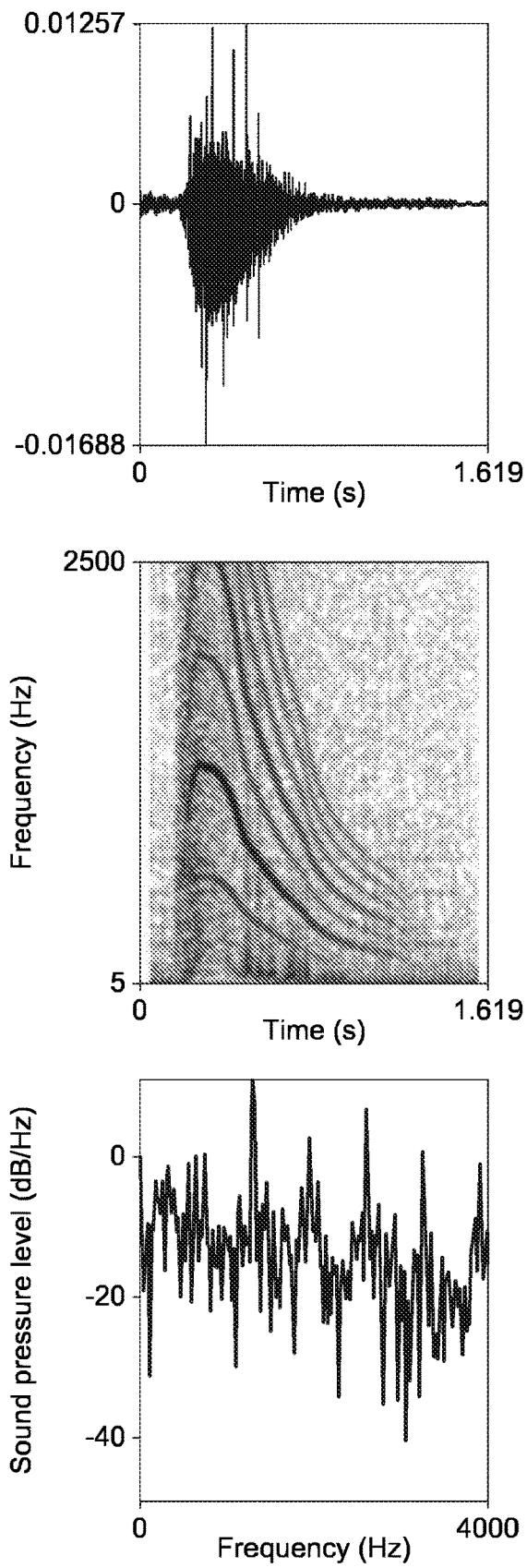
FIG. 3 shows a graphical representation of an electrical signal produced by a single exhalation into a spirometer (not claimed) as analysed using Praat software on a smartphone device. Panel 1 shows the electrical signal received at the microphone input from the device. Panel 2 shows the spectral analysis of the input. Panel 3 shows a vertical slice through the spectral chart, showing distinct maxima (visible as dark bands) at the dominant frequency (1250 Hz) and its harmonics.

Described herein is a spirometer [1] (not claimed) for measuring throughput air flow shown in FIGS. 1 to 3 features an inlet deflector [2] and an outlet deflector [3], both deflectors [2,3] comprising a conductive copper coating and configured to cause an input airflow to rotate. In other embodiments only one or more than two deflectors may be provided.

Located between the aforementioned inlet [2] and outlet [3] deflectors is a rotor [4] comprising a vane portion [5] which is also coated with copper on one side and rigidly connected to a shaft portion [6]. The rotor [4] is arranged to be caused to rotate responsive to the rotating air flow. The rotor [4] is arranged so that the end portions [7,8] of the shaft portion [6] are pivotably mounted with a clearance in respective sockets [9,10] defined at the radial centre of the deflectors [2,3], such that the vane portion [5] is mounted to rotate in the rotating airflow about an axis defined by the shaft portion [6]. The deflectors [2,3] and rotor [4] assembly are mounted in a housing (not shown in FIG. 1) which serves to retain and direct the input airflow through the deflectors [2,3] and rotor [4].

In use, the rotor [4] provides the copper coating as a conductor forming part of an electrical network [12] and is configured to operate as a switch such that the conductor switches contacts of the electrical network [12] as the rotor [4] rotates so that the rotor [4] is configured to, in use, provide an electrical signal useable to detect the rotation rate of the rotor [4]. In this embodiment, the deflectors [2,3], one side of the rotor [4] and at least part of the shaft portion [6] are coated with a conductive material (copper), and together, provide a switched conductive path for the electrical network [12].

The spirometer [1] is rigidly connected to a phone plug [13] and the electrical network [12] is connected to one or more contacts [14] of said phone plug [13] that is coupled to or rigidly connected to the spirometer [1].

In order to construct a device which operates as a switch, a conductive coating is applied to the spirometer components. To achieve this, the deflectors [2,3], shaft portion [6] and vane portion [5] are placed in a metal vapour deposition chamber with one side of the vane portion [5] and one side of the shaft portion [6] covered with insulating tape, such that these covered areas will not take on the conductive coating. Two layers of metal are applied by metal vapour deposition; a first layer of copper that provides good conductivity and a second layer of chrome-nickel that provides corrosion resistance. Therefore, the deflectors [2,3], and one side of the vane portion [5] and the shaft portion [6] take on a conductive coating of copper. Owing to a portion of the vane [5] and the shaft portion [6] not featuring a conductive coating, as the vane [5] rotates, the electrical circuit is repeatedly completed and broken when the conductive portion of the vane [5] is no longer in contact with the other components which form part of the electric network.

In our hands, the clearance provided between the end cones of the shaft and the conical sockets [9,10] is sufficient to result in a breakage of the circuit, even though the sockets [9,10] are completely covered with a conductive material. However, it is envisaged that in embodiments where the sockets [9,10] are partially coated with conductive material by the metal vapour deposition process, this may help to ensure the switching action.

In order to detect the electrical signal produced by the rotation of the vane [5], the electrical network is connected to one or more contacts [14] of a phone plug [13], which is rigidly connected to the spirometer [1]. This permits the spirometer to plug into the microphone and speaker jack of a smartphone and the phone's microphone circuit applies a bias voltage (e.g. +3V) to the electrical network of the spirometer [1].

The contacts of the electrical network are switched once per complete rotation of the vane portion [5]. Breakages of the circuit can be detected in an output signal, which when measured over time, allows a switching rate to be determined. The switching rate is then used to determine the rotation rate of the vane [5] by applying a Discrete Fourier Transform (DFT) or Fast Fourier Transform (FFT).

To circumvent activation of the smartphone's low resistance direct contact responses (below 1 k Ohm) when the rotor [4] is caused to rotate in response to the rotating airflow, a 1 k Ohm resistor [15] is incorporated into the electrical network by placing it in serial connection with the rotor [4]. This additional resistance in the electrical circuit assists with the compatibility of the spirometer [1] with the specific smartphone device [16] but may not be necessary with all electronic devices suitable for use with the invention.

Using a smartphone device [16] and the Praat software package, the rotation rate of the vane [5], can further be calibrated to give a measurement of airflow (and thus the peak expiratory flow) through the spirometer [1] from a single exhalation. An example of this is given in FIG. 3, which shows a graphical representation of an electrical signal produced by a single exhalation into a spirometer [1] of the invention as analysed using Praat software on a smartphone [16]. Panel 1 shows the electrical signal received at the microphone input from the device. Panel 2 shows the spectral analysis of the input. Panel 3 shows a vertical slice through the spectral chart, showing distinct maxima (visible as dark bands) at the dominant frequency (1250 Hz) and its harmonics. In the example shown, the area around the peak of the darkest band in Panel 2 is presented in vertical cross section in Panel 3 (rather than grayscale as in Panel 2), which shows that the peak signal frequency is 1250 Hz.

Figure 4:
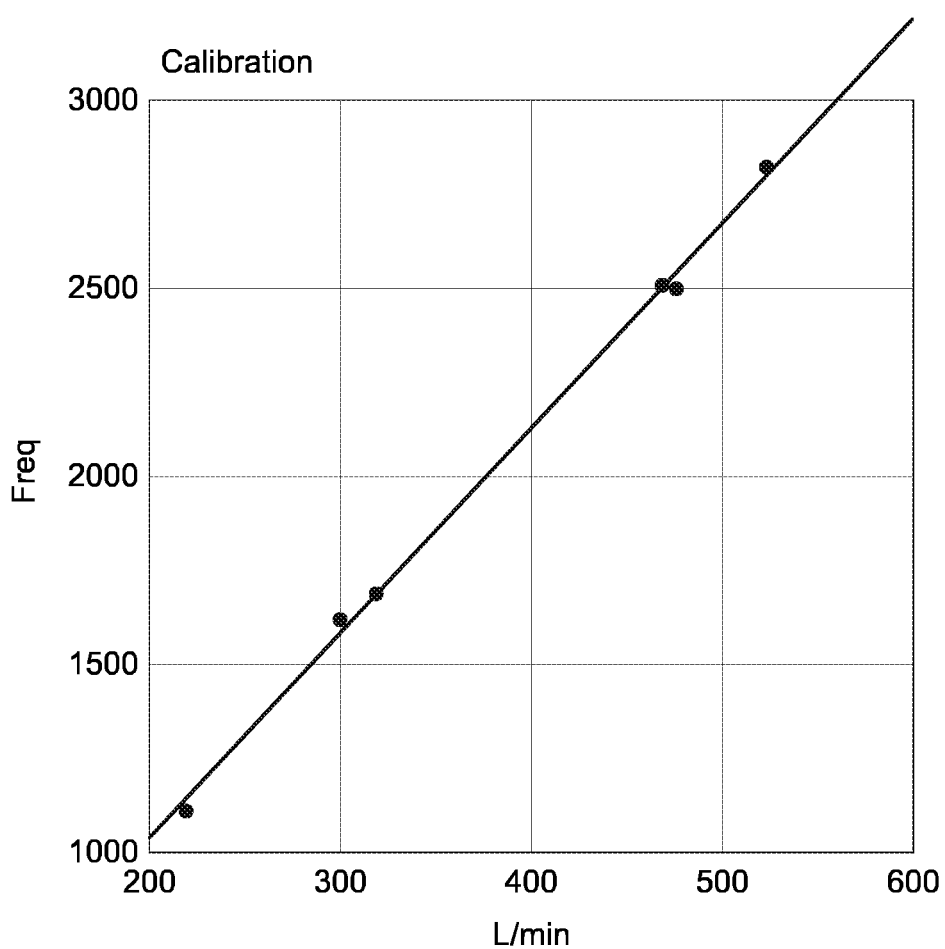
FIG. 4 shows a graphical representation of the linear relationship between signal frequency (in Hz) and flow rate (in L/min) determined from the spectral analysis of the microphone input for an example spirometer (not claimed) and produced using Microsoft Excel. In the example shown, the intercept of the X-axis corresponds to an electronic signal frequency of 1575 Hz, which corresponds to a flow rate of 300 L/min.

Although each spirometer has different characteristics and features, using exhalations of various force it is possible to calibrate the maximum signal frequency, maximum vane rotation rate and peak expiratory flow (PEF) rate for each individual spirometer. FIG. 4 shows a graphical representation of the linear relationship between signal frequency (in Hz) and flow rate (in L/min) determined from the spectral analysis of the microphone input for an example spirometer produced using Microsoft Excel. The existence of a linear relationship between these two parameters means that conversion from a maximum signal frequency to a Peak Expiratory Flow (PEF) rate which is useable by the patient (i.e. a value in L/min) requires the application of a simple multiplier. In the example shown in FIG. 4, the intercept of the X-axis at an electronic signal frequency of 1575 Hz corresponds to a flow rate of 300 L/min. The flow rate of the peak frequency (1250 Hz) shown in FIG. 3 corresponds to 240 L/min. The linear conversion of the peak harmonic frequency generated by the spirometer into flow rate described above is automatically performed by the Microsoft Excel software package, providing an output of a peak flow rate which is useable by the patient.

In addition to detecting and processing the peak of the dominant harmonic, the Microsoft Excel software package used to analyse and process the signal detects and utilises additional peaks (for example at 1.5×, 2×, 2.5× and 3× the frequency of the dominant harmonic) present in the signal output in order to determine the signal frequency of the dominant harmonic with greater accuracy and precision. For instance, these peaks are visible in Panel 3 at frequencies of, half (625 Hz), 1.5× (1875 Hz) and double (approximately 2500 Hz) that of the dominant harmonic. Application of FFT divides the spectrum between 0 and the sampling frequency (44,100 with a HD recording) into equally sized bands, for example at a resolution of 1024 bands, each band is 43 Hz wide. This permits accuracy (i.e. error margin) of 3.4% and 1.7% at frequencies of 1250 Hz and 2500 Hz respectively.

Statistical analysis of other characteristics of the spectral output (e.g. the area under the graphed flow rate line) may be used to determine other useful breathing characteristics as required.

The electrical elements provided by the rotor [4] may alternatively comprise one or more capacitance plates [17] proximate of the edge(s) of the vane portion [5] of the rotor [4], arranged partially around the periphery of the rotational edge of the vane portion [5] in order that the angle of the vane portion [5] during rotation alters the capacitance in the electrical network. Alterations in the capacitance of the electrical network may be communicated to an electronic device via a phone plug [13].

TABLE 1

Principal spirometric data from an example reference sample.

| | Males (n = 270) Mean ± SD | Males (n = 373) Mean ± SD |
|---|---|---|
| FVC (L) | 4.64 ± 0.77 | 3.14 ± 0.65 |
| $FEV_6$ (L) | 4.51 ± 0.78 | 3.11 ± 0.65 |
| $FEV_1$ (L) | 3.77 ± 0.67 | 2.56 ± 0.57 |
| $FEV_1$/FVC (%) | 81 ± 5 | 81 ± 5 |
| $FEV_1$/$FEV_6$ (%) | 82 ± 5 | 82 ± 5 |
| $FEF_{25-75}$ (L/s) | 3.87 ± 1.20 | 2.70 ± 0.94 |
| $FEF_{50}$ (L/s) | 4.82 ± 1.44 | 3.40 ± 1.14 |
| $FEF_{75-85}$ (L/s) | 1.02 ± 0.46 | 0.71 ± 0.39 |
| $FEF_{75}$ (L/s) | 1.58 ± 0.64 | 1.07 ± 0.52 |
| PEF (L/s) | 11.1 ± 1.75 | 7.14 ± 1.28 |

Figure 8:
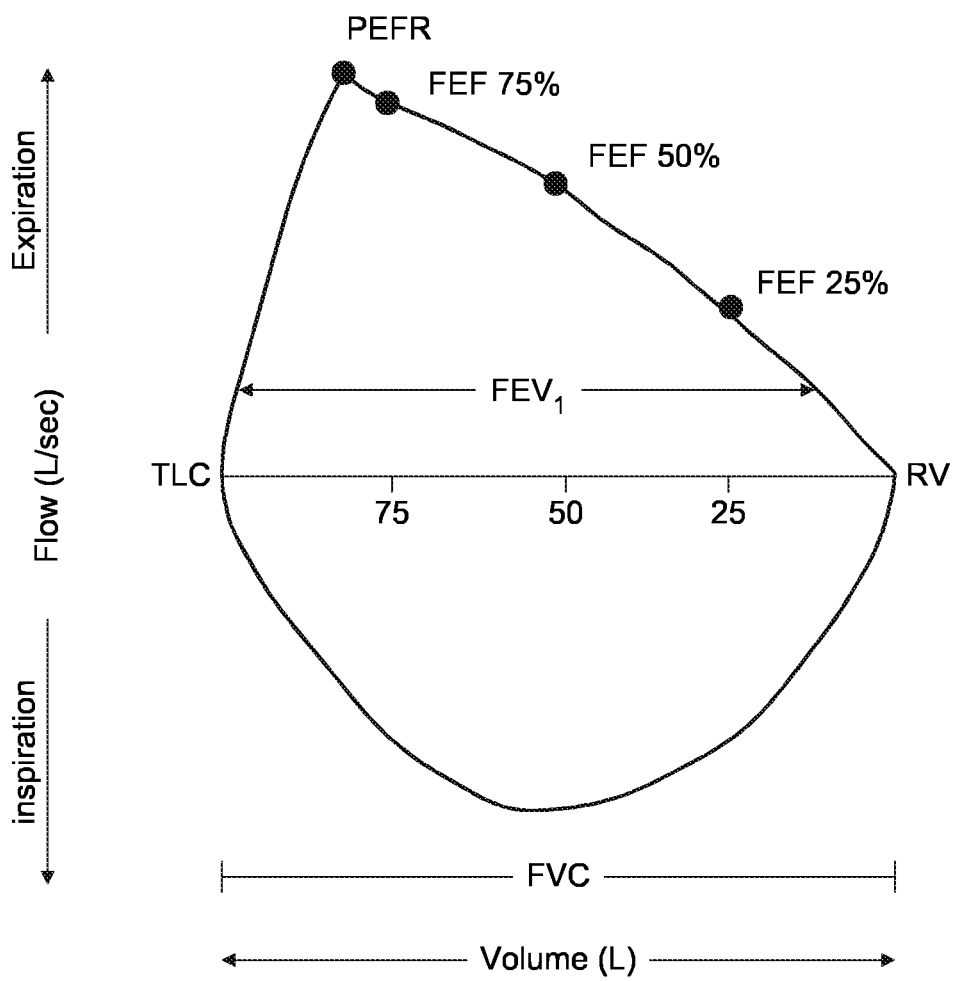
FIG. 8 shows an example graphical output of measurements derived from an exhalation (above x-axis) and inhalation (below x-axis) using a spirometer of the second and third embodiments of the invention. The exhalation produces a line which rises sharply and declines gradually. In contrast, the inhalation (below the x-axis) produces a more rounded profile. Measurement of the direction of vane rotation provides a more accurate method of determining whether the values obtained relate to exhalation or inhalation. A number of diagnostic values can be calculated from analysis of such an output. Abbreviations; $FEV_1$; Forced Expiratory Volume in 1 second, FEF; Forced Expiratory Flow, $FEF_{75\%}$; Forced Expiratory Flow, at 75% of the total expired volume, $FEF_{50\%}$ Forced Expiratory Flow at 50% of the total expired volume; $FEF_{25\%}$; Forced Expiratory Flow at 25% of the total expired volume, FVC; Forced Vital Capacity (zero flow reached), PEFR; Peak Expiratory Flow Rate, RV; Residual Volume; TLC; Total Lung Capacity.

With reference to FIG. 8, it can be seen that this table demonstrates obstructive and restrictive lung function impairment. In restrictive lung function impairment, the total lung capacity (FVC; Forced Vital Capacity) is reduced. In obstructive the total capacity is more or less unchanged, but it takes longer to exhale the air through the restricted airways. $FEV_1$/$FEV_6$; the ratio of the amount of air exhaled in one second and six seconds is a standard proxy for implant rejection. Abbreviations; SD; Standard Deviation, $FEV_1$; Forced Expiratory Volume in 1 second, $FEV_6$; Forced Expiratory Volume in 6 seconds, $FEF_{25-75}$; Forced Expiratory Flow between 25 and 75%, $FEF_{50}$; Forced Expiratory Flow at 50%, $FEF_{50}$; Forced Expiratory Flow at 75%, $FEF_{75-85}$; Forced Expiratory Flow between 75 and 85%, FVC; Forced Vital Capacity, PEF; Peak Expiratory Flow.

Figure 6:
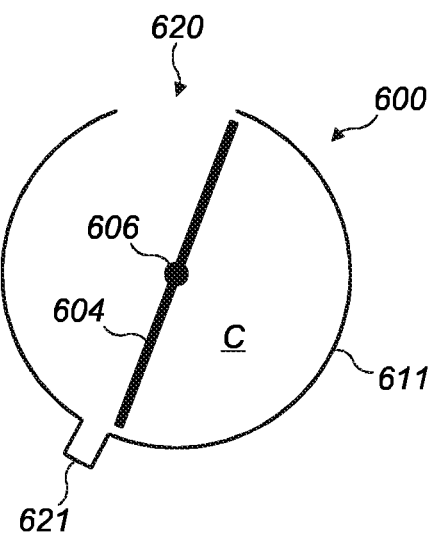
FIG. 6 shows a transverse section of a spirometer in accordance with a third embodiment of the invention in particular, showing a single photodetector (photodiode) (D1) positioned 'offset' from 180 degrees relative to the position of the window (gap) in the cylindrical wall of the spirometer and the rotor. In addition to the rate of rotation, this arrangement permits the direction of rotation (A; clockwise, B; anti-clockwise) to be measured.
Figure 7A:
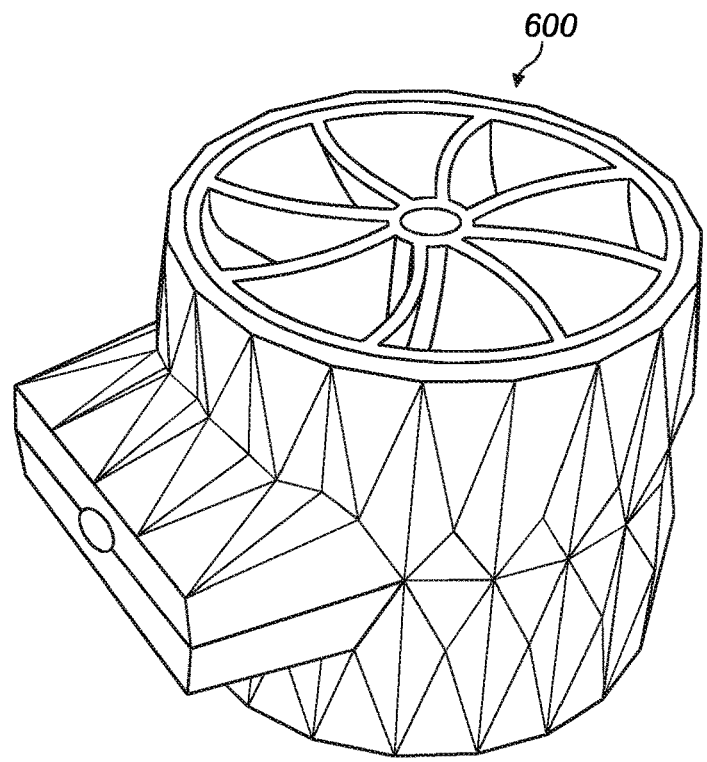
FIG. 7 shows perspective views of a design of a spirometer of the third embodiment of the invention. Panel A shows the microphone plug. Panel B shows an external view of the window in the cylindrical wall.
Figure 7B:
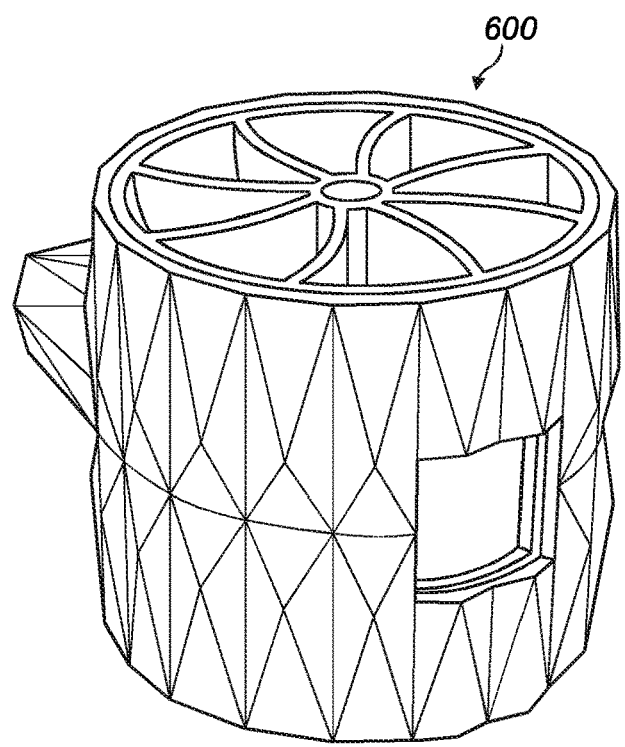
Figure 12:
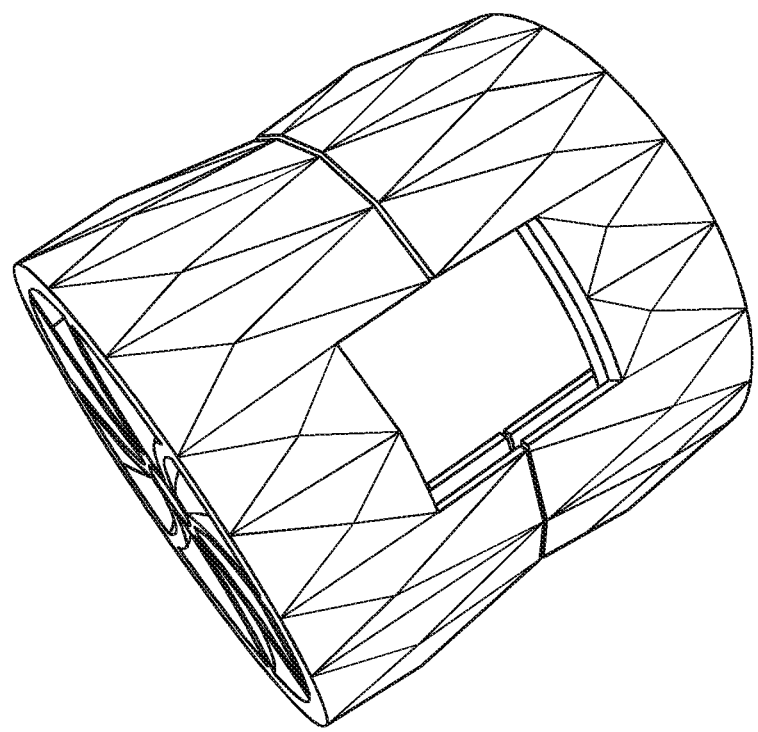
FIG. 12 shows a view of a window of a spirometer manufactured in accordance with the third embodiment of the invention.
Figure 13:
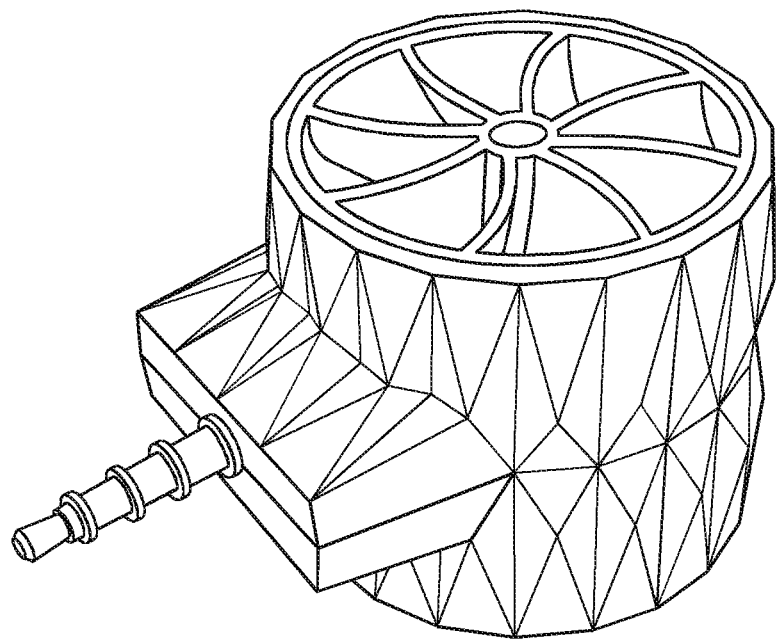
FIG. 13 shows a view of an assembled spirometer of FIG. 12 having a phone plug connector for connecting to a smartphone.

Aspects of the invention will now be described with reference to FIGS. 5 to 14. A first embodiment of a spirometer [500] is illustrated in particular in FIG. 5, whereas a second embodiment [600] is illustrated in FIG. 6 and shown in more detail shown in particular in FIGS. 7 and 12 to 14. FIG. 7 shows perspective views of a design of a spirometer of the third embodiment of the invention, whereas FIGS. 12, 13 and 14 illustrate the assembly of a spirometer manufactured according to this design.

Figure 14:
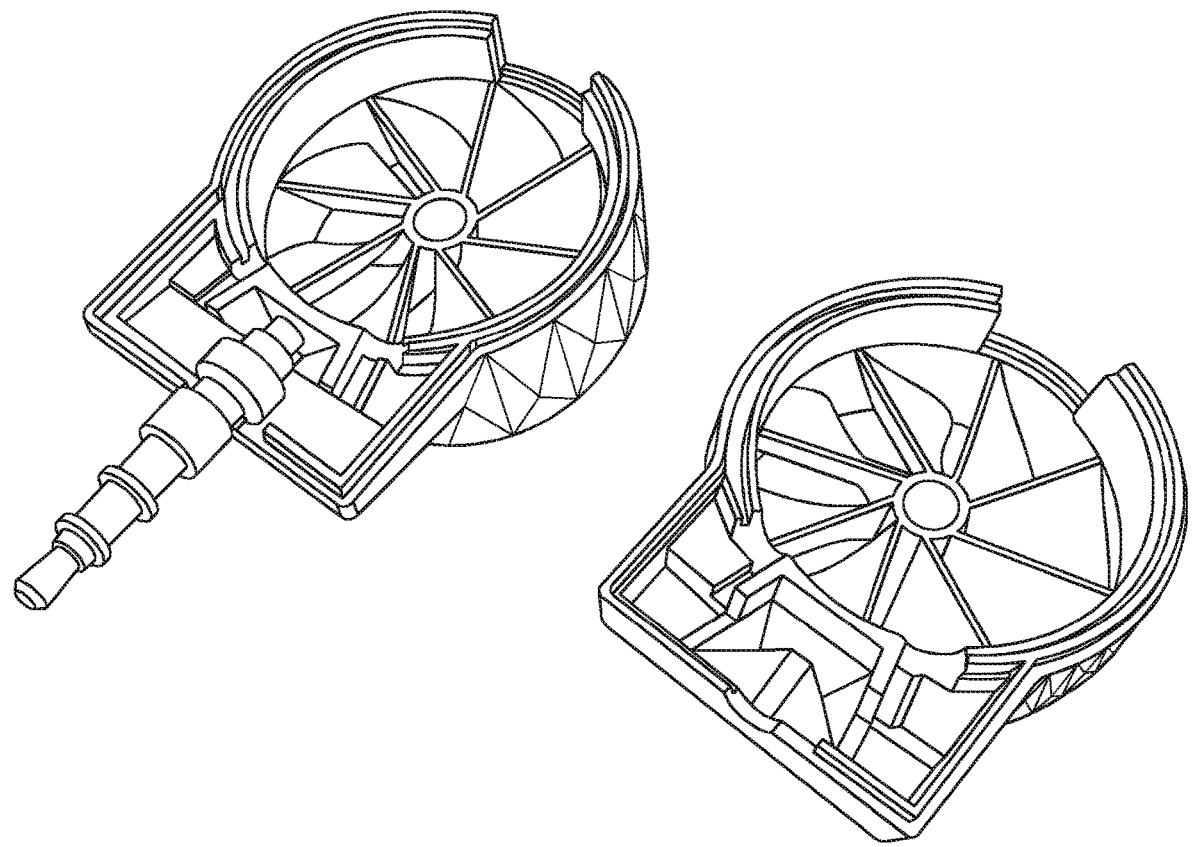
FIG. 14 shows a view of the two halves of the housing of the spirometer of FIGS. 12 and 13 during assembly.

In these alternative embodiments the spirometer [500], [600] of the invention for measuring throughput air flow shown in FIGS. 4 to 14 features an inlet deflector and an outlet deflector (shown only in FIG. 14 for the third embodiment). Both deflectors have curved spokes and are configured to cause an input airflow to rotate. In other embodiments only one or more than two deflectors may be provided.

Located between the aforementioned inlet and outlet deflectors is a rotor [504, 604] comprising a vane portion made of opaque plastics material, which is rigidly connected to a shaft portion [506, 606]. The rotor [504, 604] is arranged to be caused to rotate responsive to the rotating air flow. The rotor [504, 604] is arranged so that the end portions of the shaft portion [506, 606] are pivotably mounted in respective sockets (see FIG. 14, for the third embodiment only) defined at the radial centre of the deflectors, such that the vane portion is mounted to rotate in the rotating airflow about an axis defined by the shaft portion [506, 606]. The deflectors and rotor [504, 604] assembly are mounted in a housing [511, 611] which serves to retain and direct the input airflow through the deflectors and rotor [504, 604]. The housing [511, 611] comprises a cylindrical wall made of opaque plastics material, defining a cavity C and having a window [520, 620] provided therein, arranged to admit ambient light to the cavity. In other embodiments, plural windows may be provided side-by-side in an axial or tangential direction.

Located in respective recesses in the cylindrical wall of the housing [511, 611] is one or more photodiodes [521D$_1$, 521D$_2$, 621D], arranged at the wall facing into the cavity to detect an amount of light incident thereon inside the cavity.

The spirometer [500, 600], and in particular, the window(s) [520, 620], cavity, rotor [504, 604] and photodiode(s) [521D$_1$, 521 D$_2$, 621D] thereof, is configured such that, as the angle of the rotor [504, 604] changes as it rotates, the amount of the ambient light admitted to the cavity by the one or more windows [520, 620] and conveyed to the photodiode(s) [521D$_1$, 521D$_2$, 621D] is varied due to obstruction by the rotor [504, 604].

The photodiode(s) [521D$_1$, 521D$_2$, 621D] forms part of an electrical network configured to, in use, provide an electrical signal representative of the variation of photocurrent from the or each of the photodiode(s) [521D$_1$, 521 D$_2$, 621D] over time as the rotor rotates due to the airflow. The electrical signal is useable to detect the rotation rate and direction of rotation of the rotor.

The cavity of the spirometer body defines a first radius and the radial extent of the vanes defines a second radius. The axial extent of the rotor [504, 604] (the second radius) is substantially the same as the axial extent of the cavity so as to allow it to block light within the cavity from reaching the photodiode when the vane is interposed between the window and the photodiode. However, the radial extent of the vanes [505, 605] is marginally less than the first radius allowing free rotation of the rotor [504, 604] within the cavity. The axial extent of the window [520, 620] is less than and contained within the axial extent of the rotor [504, 604], which allows optimal occlusion of the window from the photodiode when the vane is interposed between the two.

Besides rotation rate sensitivity, the spirometers of the second and third embodiments provide directional sensitivity usable to distinguish inhalation and exhalation cycles. This can be achieved in a number of ways.

Figure 5:
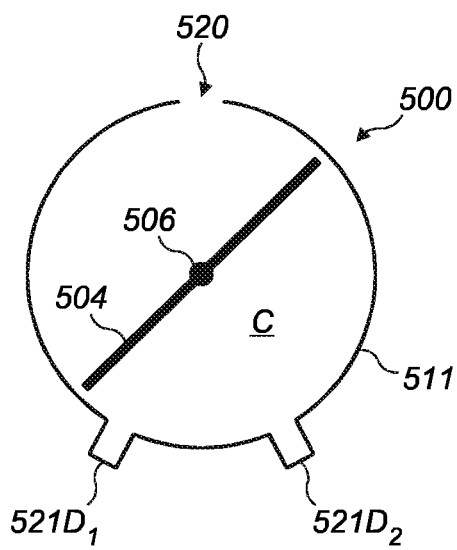
FIG. 5 shows a transverse section of a spirometer in accordance with a second embodiment of the invention, in particular, showing the location of two photodetectors (photodiodes) (D1 and D2) relative to the position of the window (gap) in the cylindrical wall of the spirometer and the rotor.

In the first embodiment, shown in FIG. 5, the cylindrical wall of the spirometer has a single window [520] and multiple, in this case two, photodiodes [521D$_1$, 521D$_2$] arranged to be spaced at angles to each other relative to the window [520]. The photocurrent produced by the photodiodes [521D$_1$, 521D$_2$] as the rotor [504] rotates is staggered in time, the ordering of which reveals the direction of rotation. For example, when the rotor [504] rotates in an anti-clockwise direction during inhalation, the photocurrent produced by photodiode 521D$_1$ peaks first, followed shortly by the photocurrent produced by the other photodiode 521 D$_2$, after which they both are not illuminated and so do not produce any photocurrent. On exhalation, the ordering of the peaks is reversed as the rotor [504] then rotates in the clockwise direction.

Figure 10:
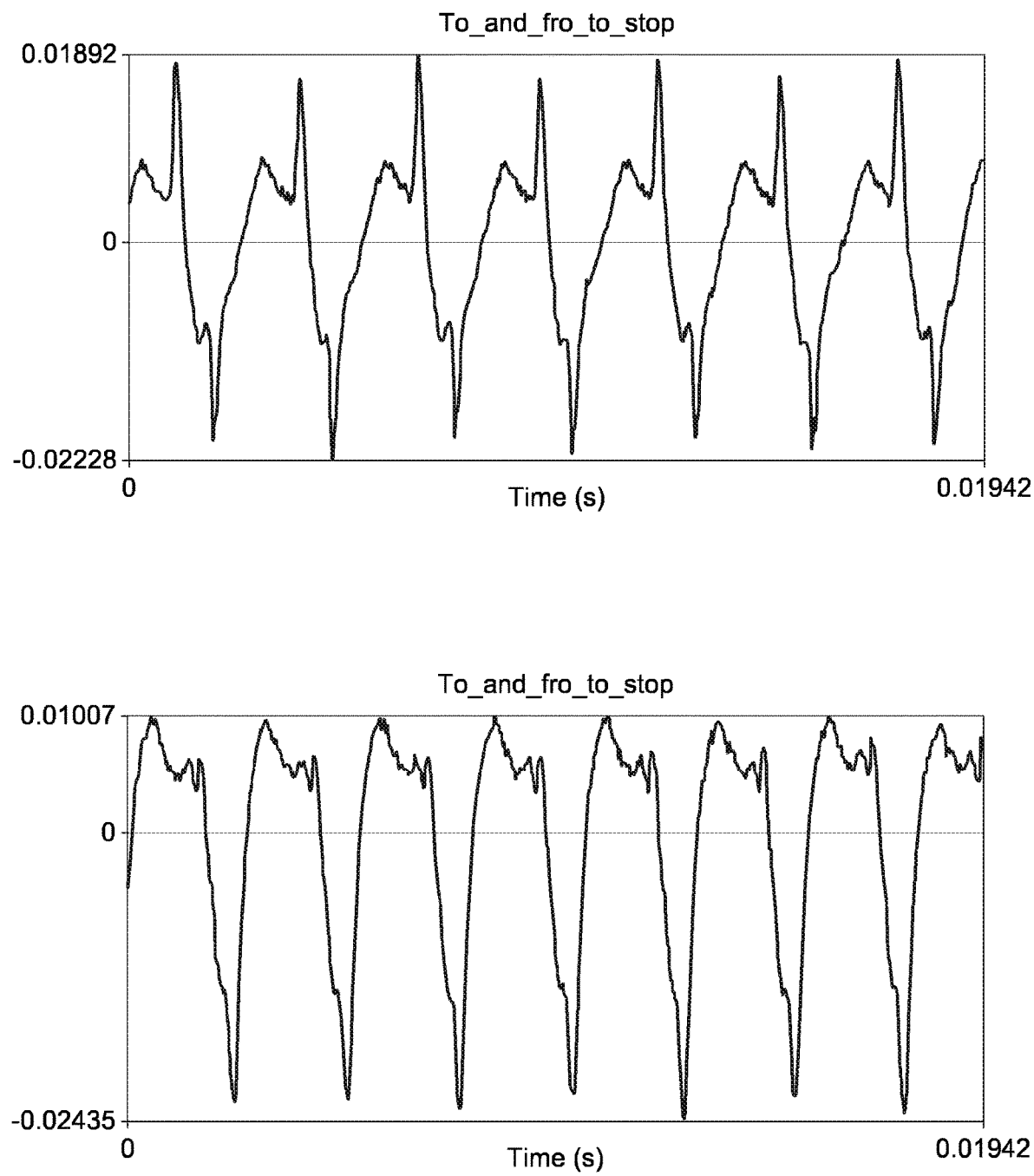
FIG. 10 shows a graphical representation of the different signals detected by the microphone of a smartphone electronic device with the rotor of the spirometer spinning clockwise (top panel) and anti-clockwise (bottom panel).

In the second embodiment, shown in FIG. 6, the cylindrical wall of the spirometer 600 comprises a single window [620] and a single photodiode [621D]. In order to construct a device which is capable of providing directional sensitivity as well as rotation rate, the window [620] is greater in angular or tangential extent than the light collecting or light sensitive area of the photodiode [621D] and the angle subtending between the centre of the window [620]—the axis of the rotor [604] and the centre of the photodiode [621D] is less than 180 degrees. This results in unequal periods of less than full exposure of the photodiode [621D] to the window [620] during the passage of the vane [605] leading to a sawtooth pattern in the light intensity illuminating the photodiode [621D] (see FIG. 10). Whether the leading edge of the sawtooth pattern is sharp or sloped depends on the direction of rotation of the rotor [604]. The characteristics and shape of this sawtooth pattern is detectable in the electrical signal output. As shown in FIG. 10, electrical signal produced at the smartphone by clockwise rotation is shown in the top panel, whereas the signal produced by anti-clockwise rotation is shown in the bottom panel. The biasing and circuitry in the electrical network slightly distorts the signal produced at the smartphone such that the form of the signals looks quite different. But nevertheless, it is possible to tell from the signal alone the direction of rotation, which permits the direction of rotation of the rotor in response to throughput air as well as the rate of rotation to be detected, which allows airflow due to inhalation and exhalation to be distinguished. In the second embodiment, the window [620] is rectangular in shape, having uniform axial length across its angular extent. In alternative embodiments, multiple windows may be provided. Alternatively, or in addition, the or each window may have a non-uniform shape, which may have a varying axial length along its angular extent. For example, by providing a window that has a triangular shape, the sawtooth shape of the produced photocurrent signal may be more pronounced and more easily detectable.

In use, the photodiode [621D] forms part of an electrical network coupled to the photodiode and configured to, in use, provide an electrical signal useable to detect the light level reaching the photodiode [621D] and thus, the rotation rate and direction of the rotor [604]. As the rotor [604] rotates the amount of illumination incident upon the photodiode [621D] varies. Alterations in the light level reaching the photodiode [621D] are transduced into an electrical signal, which may be communicated to an electronic device via a phone plug [13].

The spirometer [500, 600] is rigidly connected to a phone plug (not shown for the first embodiment) and the electrical network is connected to one or more contacts of said phone plug that is coupled to or rigidly connected to the spirometer [500, 600].

In order to detect the electrical signal produced by the rotation of the vane, the electrical network is connected to one or more contacts of a phone plug, which is rigidly connected to the spirometer [500, 600]. This permits the spirometer [500, 600] to plug into the microphone and speaker jack of a smartphone and the phone's microphone circuit applies a bias voltage (e.g. +3V) to the electrical network of the spirometer [500, 600].

In the second embodiment, as shown in the top panel of FIG. 10 the raw electrical signal produced in the electrical network due to the photocurrent produced by the photodiode exhibits a sawtooth peak twice per complete rotation of the vane portion [604]. Due to the bias voltage applied by the smartphone's microphone circuit the raw signal shown at FIG. 10 is above and below a zero level. The sawtooth pattern of the circuit can be detected in an output signal, which when measured over time, allows a rotation rate of the rotor [605] to be determined for example by applying a Discrete Fourier Transform (DFT) or Fast Fourier Transform (FFT).

To circumvent activation of the smartphone's low resistance direct contact responses (below 1 k Ohm) when the rotor [605] is caused to rotate in response to the rotating airflow, like in the first embodiment a 1 k Ohm resistor (not shown) is incorporated into the electrical network by placing it in serial connection with the photodiode [621D]. This additional resistance in the electrical circuit assists with the compatibility of the spirometer [600] with the specific smartphone device but may not be necessary with all electronic devices suitable for use with the invention.

Using a smartphone device and the Praat software package, the rotation rate of the vane [605], can further be calibrated to give a measurement of airflow (and thus the peak expiratory flow, forced expiratory volume, forced expiratory flow and forced vital capacity) through the spirometer [600] from a single exhalation or inhalation. Signal processing has the following elements; the change in microphone signal intensity can show individual rotations (FIG. 10), autoregressive analysis can be used to detect repetition in the signal pattern, Discrete Fourier Transform (DFT) can be used as a faster way of counting many peaks and signal shape analysis can be used to recognise forward and backward rotation.

Figure 11:
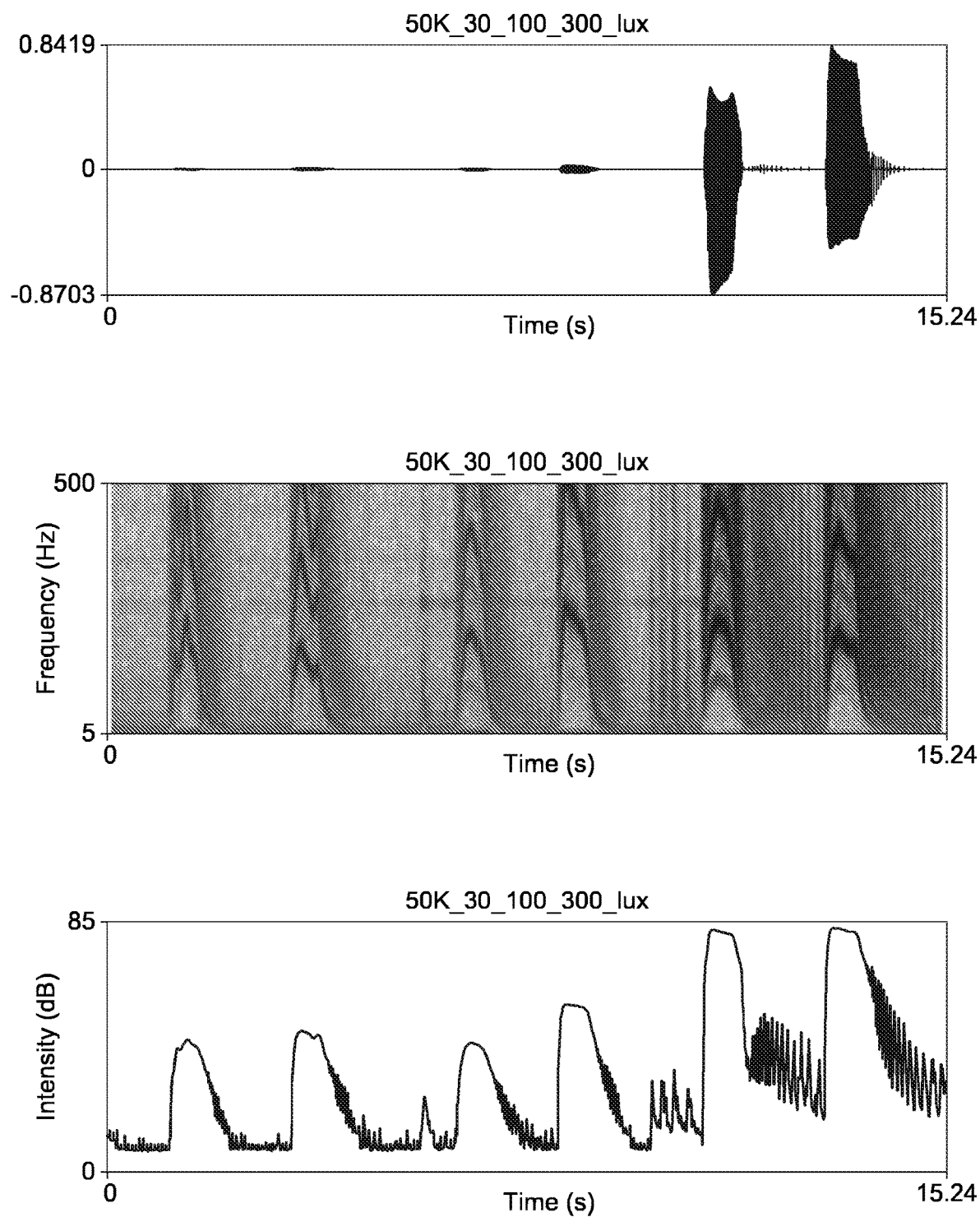
FIG. 11 shows a graphical representation of raw signals (top panel), spectrum (middle panel) and intensity (bottom panel) at three subsequently increasing levels of lighting, with a forward and backward spin at each level. At high revolutions signal processing by Discrete Fourier Transform (DFT) is used to determine rotations per second. At low revolutions the signal intensity is used to determine individual on-off signals. Detection of direction of rotation optimally occurs where the signal is strongest (rotation is fastest) in the inhale-exhale cycle.

An example of this is given in FIG. 11, which shows a graphical representation of an electrical signal produced by exhalation and inhalation into a spirometer [600] of the third embodiment of the invention in three different, increasing light levels as analysed using Praat software on a smartphone. Panel 1 shows the raw electrical signal received at the microphone input from the device. Panel 2 shows the spectral analysis of the electrical signal using a Discrete Fourier Transform algorithm (DFT). Panel 3 shows the signal intensity. At high frequencies, it is possible to determine the rotation rate of the spirometer vane [605] using the spectral analysis produced by the DFT. At low frequencies, it may be necessary to determine the rotation rate from the peaks in the signal intensity. From this it is possible to determine the airflow through the spirometer [600] in litres/min.

As with the spirometer shown in FIGS. 1-4, although each spirometer of the first and second embodiments, has different characteristics and features, using exhalations of various force it is possible to calibrate the maximum signal frequency, maximum vane rotation rate peak expiratory flow rate, forced expiratory volume, forced expiratory flow and forced vital capacity for each individual spirometer.

Statistical analysis of other characteristics of the spectral output (e.g. the area under the graphed flow rate line) may be used to determine other useful breathing characteristics as required.

A method of manufacturing a spirometer [500, 600] for measuring throughput air flow according to the first and second embodiments will now be described with particular reference to FIGS. 12, 13 and 14.

Firstly, the method includes providing a spirometer body [511, 611] having a cylindrical wall defining a cavity and having one or more windows [520, 620] arranged to admit ambient light to the cavity. The spirometer body [511, 611] or housing may be provided in two halves, as shown in FIG. 14. The spirometer body may be produced, for example, by a plastics moulding process.

Figure 9:
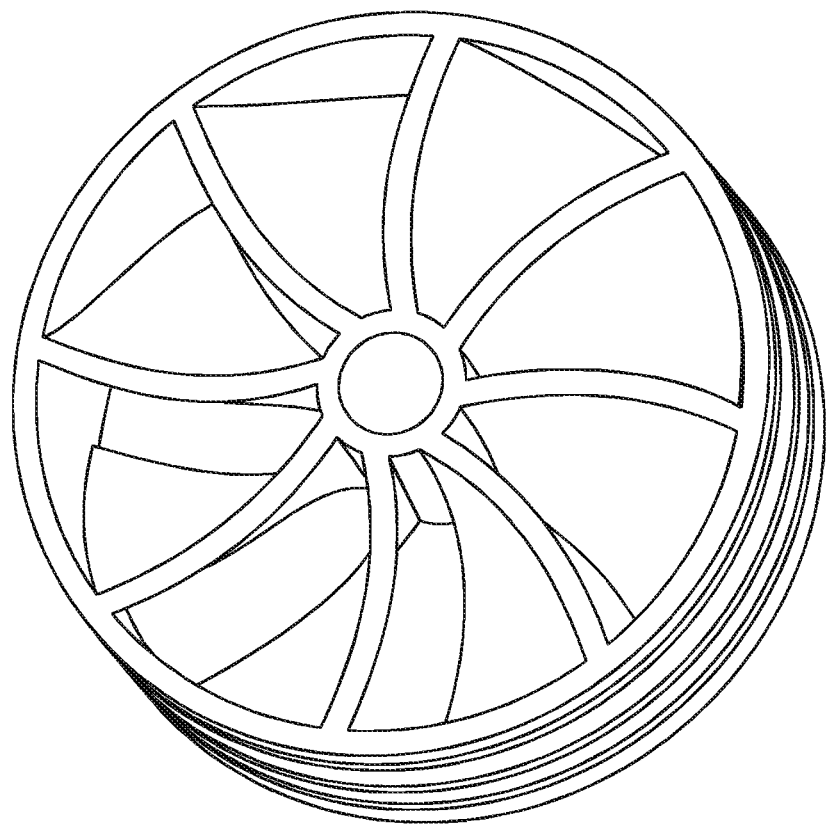

Next, the method includes providing, inlet and outlet deflectors as shown in FIG. 9 configured to cause an input airflow to the cavity defined by the spirometer body to rotate and a rotor [504, 604] comprising a vane portion rigidly connected to a shaft portion [506, 507].

Then, the method includes providing one or more photodetectors arranged at the wall of the spirometer body [511, 611] facing into the cavity to detect an amount of light incident thereon inside the cavity.

Then, the method includes forming part of an electrical network, coupled to the or each photodetector and configured to, in use, provide an electrical signal useable to detect the rotation rate of the rotor [504, 604].

The method then includes coupling or rigidly connecting a phone plug to the spirometer and connecting the electrical network to one or more contacts of the phone plug that is coupled to or rigidly the spirometer [500, 600]. As shown in FIG. 14, the phone plug may be arranged in and supported between parts of two halves of housing [511, 611].

The method also includes assembling the rotor between the inlet and outlet deflectors such that the end portions of the shaft [506, 606] are pivotably mounted in respective sockets defined at the radial centre of the deflectors, such that the vane portion is mounted to rotate in the rotating airflow such that, in use as the angle of the rotor [504, 604] changes as it rotates the amount of the ambient light admitted to the cavity by the one or more windows [520, 620] and conveyed to the or each photodetector is varied due to obstruction by the rotor [504, 604]. This assembly may be achieved, by, for example, bringing together the two halves of the housing shown in FIG. 14 to suspend the rotor [504, 604] therebetween. A transparent plastic window may be inserted in the gap G moulded in the housing halves to provide the window. The assembled spirometer is shown in FIG. 13, and the window [620] is shown in detail in FIG. 12.

The invention claimed is:
1. A spirometer for measuring throughput airflow comprising:
    a spirometer body having a cylindrical wall defining a cavity and having one or more windows arranged to admit ambient light to the cavity;
    one or more deflectors configured to cause an airflow input to the cavity defined by the spirometer body to rotate;
    a rotor arranged inside the cavity defined by the spirometer body to be caused to rotate responsive to the rotating airflow; and
    one or more photodetectors, arranged at the wall of the spirometer body facing into the cavity to detect an amount of light incident thereon inside the cavity;
    wherein the spirometer is configured such that, as an angle of the rotor changes as it rotates, the amount of the ambient light admitted to the cavity by the one or more windows and conveyed to the or each photodetector is varied due to obstruction by the rotor; and wherein the one or more photodetectors form part of an electrical network configured to, in use, provide an electrical signal useable to detect the rotation rate of the rotor.

2. A spirometer as claimed in claim 1, wherein the electrical network is connected to one or more contacts of a phone plug that is coupled to, or rigidly connected to the spirometer.

3. A spirometer as claimed in claim 1, wherein the rotor comprises a vane portion rigidly connected to a shaft portion such that the vane portion can rotate about an axis defined by the shaft portion; and
wherein both end portions of the shaft portion are pivotably mounted in respective sockets of the spirometer, such that the vane portion is mounted to rotate in the rotating airflow.

4. A spirometer as claimed in claim 3, wherein the one or more photodetectors are arranged partially around a periphery of a surface bounded by rotational edges of the vane portion.

5. A spirometer as claimed in claim 4, wherein the one or more photodetectors are located in recesses in the wall of the spirometer body facing into the cavity.

6. A spirometer as claimed in claim 5, wherein the cavity of the spirometer body defines a first radius and a radial extent of the vane portion defines a second radius; and wherein the second radius is such as to allow it to block light within the cavity from reaching the one or more photodetectors but less than the first radius allowing free rotation within the cavity.

7. A spirometer as claimed in claim 6, wherein an axial extent of the or each window is less than and contained within an axial extent of the rotor.

8. A spirometer as claimed in claim 7, wherein the axial extent of the rotor is substantially the same as an axial extent of the cavity.

9. A spirometer as claimed in claim 1, wherein the cylindrical wall comprises a single window and a single photodetector.

10. A spirometer as claimed in claim 1, wherein the cylindrical wall comprises a single window and a plurality of photodetectors.

11. A spirometer as claimed in claim 10, wherein the photodetectors in the plurality of photodetectors are spaced at angles around the cylindrical wall.

12. A spirometer as claimed in claim 1, wherein at least one of the one or more photodetectors is a photodiode.

13. A spirometer as claimed in claim 1, wherein the cylindrical wall of the spirometer is opaque except for the one or more windows arranged to admit ambient light to the cavity.

14. A spirometer as claimed in claim 1, wherein the spirometer is connected to an electronic device.

15. A spirometer as claimed in claim 1, wherein the light incident on the one or more photodetectors is not provided by active or powered light source.

16. A spirometer as claimed in claim 1, wherein the electrical network comprises one or more resistors.

17. A spirometer as claimed in claim 16 wherein the one or more resistors are in the range 500 Ohm-3 k Ohm and in serial connection with the rotor.

18. A method of measuring throughput airflow using a spirometer as claimed in claim 1, comprising the steps of:
a. connecting the spirometer to an electronic device; and
b. detecting, using the electronic device, the electrical signal provided by the spirometer experiencing the airflow therethrough; and
c. processing, using the electronic device, the electrical signal to obtain a measurement of a characteristic of the throughput airflow.

19. A method as claimed in claim 18, wherein processing, using the electronic device, the electrical signal comprises determining a rotation rate of the rotor from a component of the electrical signal produced by the operation of the one or more photodetectors as the rotor rotates.

20. A method of detecting throughput airflow as claimed in claim 19, wherein processing, using the electronic device, the electrical signal further comprises the step of performing a Discrete Fourier Transform (DFT) to convert a component of the electrical signal produced by the operation of the one or more photodetectors as the rotor rotates into a rotation rate.

21. A method as claimed in claim 18, wherein processing, using the electronic device, the electrical signal comprises determining characteristics of the airflow from a determined rotation rate of the rotor, based on calibration data defining relationships therebetween for the spirometer.

22. A method as claimed in claim 18, wherein processing, using the electronic device the electrical signal further comprises determining the direction of rotation of the rotor.

23. A method of manufacturing a spirometer, comprising:
a. Providing a spirometer body having a cylindrical wall defining a cavity and having one or more windows arranged to admit ambient light to the cavity;
b. providing inlet and outlet deflectors configured to cause an input airflow to the cavity defined by the spirometer body to rotate and a rotor comprising a vane portion rigidly connected to a shaft portion;
c. providing one or more photodetectors arranged at the wall of the spirometer body facing into the cavity to detect an amount of light incident thereon inside the cavity;
d. forming part of an electrical network, coupled to the or each photodetector and configured to, in use, provide an electrical signal useable to detect the rotation rate of the rotor;
e. assembling the rotor between the inlet and outlet deflectors such that both end portions of the shaft portion are pivotably mounted in respective sockets defined at a radial center of the deflectors, such that the vane portion is mounted to rotate in the rotating airflow such that, in use as an angle of the rotor changes as it rotates the amount of the ambient light admitted to the cavity by the one or more windows and conveyed to the or each photodetector is varied due to obstruction by the rotor; and
f. coupling or rigidly connecting a phone plug to the spirometer and connecting the electrical network to one or more contacts of the phone plug that is coupled to or rigidly connected to the spirometer.

* * * * *